United States Patent [19]

Bennett

[11] Plant 4,730

[45] Jun. 2, 1981

[54] MINIATURE ROSE PLANT

[76] Inventor: Cecilia L. D. Bennett, 489 Minot Ave., Chula Vista, Calif. 92010

[21] Appl. No.: 134,940

[22] Filed: Mar. 28, 1980

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant characterized by the pink with darker reverse flowers and bloom form.

1 Drawing Figure

1

The present invention relates to a new and distinct variety of a bush type rose plant of miniature class; the variety showing a strong resemblance to its seed parent, Gene Boerner, a floribunda variety (U.S. Plant Pat. No. 2,885).

The variety is further characterized by:

An abundance of blooms, borne singly or in clusters, held very erect and well above foliage.

Has a slight fragrance.

The plant is vigorous, with an open airy appearance. The foliage is small and glossy with a touch of red or bronze on edge of leaflets; the buds and flowers are very similar to Gene Boerner, a medium pink with a deeper reverse, outer petals quilling as bloom matures.

The plant ranges in size from 12–18 inches, will get slightly larger when planted in the ground.

The plant has good growing habits, well shaped and attractive in appearance. Blooms held erect on tall stems. Plant will bloom singly or have up to seven blooms per stem.

The present variety of miniature rose was originated by me at Tiny Petal's Nursery located at Chula Vista, Calif., under careful observation, and is a cross of Elfinesque, a miniature as the pollen parent and Gene Boernor (U.S. Plant Pat. No. 2,885) the seed parent.

Subsequent to origination of the variety I successfully reproduced it at Tiny Petal's Nursery located at aforesaid with reproductions coming true in all respects.

The color photographs illustrate the variety.

Referring now specifically to the new and distinct variety of miniature rose plant, the following is a detailed description thereof in outline; all major color plate identifications being by reference to the New England Gladiolus Society Fischer Color Chart. Color chart used except where common terms of color definition are employed.

Type: Miniature; hardy; bushy; seedling; greenhouse; potted plant; garden decoration; cut flowers; exhibition.

Class: Miniature—Variety name "Cissie".

Flowers borne: Singly or in clusters of up to seven blooms to a stem.

Quantity of bloom: Abundant both outside and in the greenhouse.

Bud:

*Peduncle.*—Short to medium in length; slender but sturdy; erect; hairs—fairly numerous; reddish.

*Before calyx breaks, size.*—Small. Form elongated; pointed with several foliaceous appendages extending beyond the tip of the bud and on bud surface. Color—medium pink. R 5. on the Fischer color chart.

2

Bloom:

*Size when fully open.*—Small, averaging about 35–40 mm (1½"). Petalage—double—averaging about 20 petals, arranged evenly. Form—pointed, with petals opening symmetrically, outer petals quilling as the bloom opens.

Petals: Fairly thick; satiny on inside and outside of petals.

*Shape.*—Outside petals, broad lanceolate with round tip plus very small (short) acute tip; inside—lanceolate with rounded tip.

Color: Newly opened flower from a plant grown outdoors, Chula Vista, Calif.

Outside petals:

*Outside surface.*—Medium pink. R 5. Fischer color chart.

*Inside surface.*—Medium pink. R 6. Fischer color chart.

Intermediate petal:

*Outside petal surface.*—Similar to outside petal.

*Inside petal.*—Similar to outside petal.

Inner petal:

*Outside surface.*—Same as intermediate petal; inside petal surface—same as intermediate petal. General color effect; newly opened flowers—vibrant pink. Three days open—color similar to newly opened flowers. Blooms last exceptionally well and retain good color.

Reproductive organs:

*Stamens.*—Abundant, arranged regularly around pistil.

*Filaments.*—Varying length, fairly long, yellow.

*Anthers.*—Well formed; yellow.

*Pollen.*—Moderate amount.

*Pistils.*—Average number.

*Styles.*—Fairly even; medium to short, bunched; color—delicate green.

*Ovaries.*—All enclosed in calyx.

*Hips.*—Some.

*Sepals.*—Spear shaped; medium green, reddish tinge. reflexes when open.

*Seed.*—Some.

Foliage:

*Leaves.*—Compound of five (sometimes three or seven) leaflets; small; leathery; semi-glossy.

*Leaflets.*—Shape: broad, nearly oval; apex acute; base rounded. Margin serrated.

*Color.*—Medium green; new growth—reddish green to red.

*Rachis.*—Medium strength; upper side grooved; under side sparsely thorny with a few tiny prickles.

*Stipules.*—Medium long; narrow to medium width; medium length; narrow pointed, curves out at about a 45 degree angle.

Growth:

*Habit.*—Dwarf; bushy; much branched.

*Growth.*—Free vigorous; internodes short.

*Canes.*—Medium; slender; sturdy.

*Main stems.*—Color: reddish green.

*Thorns.*—Average; slender; straight; color, reddish.

*Branches.*—Color: medium green with a reddish tinge.

*Thorns.*—Moderate number; medium length; slender; nearly straight, inclined downward. Small oval base. Prickles: none.

The miniature rose plant and its flowers as herein described may vary in slight detail due to climatic, soil and cultural conditions under which the variety may be grown; the present description being of the variety as grown at Chula Vista, Calif.

The following is claimed:

1. A new and distinct variety of miniature rose plant of hardy, dwarf, bushy, much branched habit, substantially as illustrated and described, characterized by bud and flowers of a medium pink color, being of a shade of medium pink, (R. 5) Fischer color chart; easy to propagate from cuttings or budding, with ample supply of foliage to produce an attractive plant with an abundance of flowers; singly or in large sprays on long stems usually held high above plant.

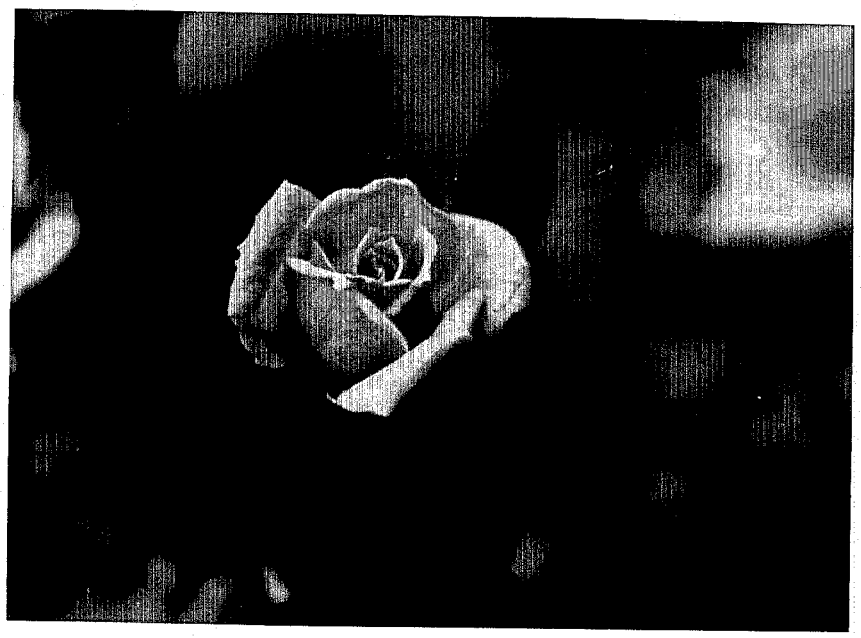

* * * * *